(12) United States Patent
Tomoda et al.

(10) Patent No.: US 6,552,198 B1
(45) Date of Patent: Apr. 22, 2003

(54) METHOD OF STABILIZING AQUEOUS PYRAZOLOACRIDONE DERIVATIVE SOLUTION

(75) Inventors: Yutaka Tomoda, Shizuoka (JP); Nobuhito Ashikawa, Shizuoka (JP); Yasuki Kato, Shizuoka (JP); Kunio Ito, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/807,211

(22) PCT Filed: Oct. 13, 1999

(86) PCT No.: PCT/JP99/05643

§ 371 (c)(1),
(2), (4) Date: Apr. 11, 2001

(87) PCT Pub. No.: WO00/21962

PCT Pub. Date: Apr. 20, 2000

(30) Foreign Application Priority Data

Oct. 14, 1998 (JP) ............................................. 10-291674

(51) Int. Cl.$^7$ ............................................. C07D 471/06
(52) U.S. Cl. ........................................... 546/66; 546/62
(58) Field of Search ...................................... 546/66, 62

(56) References Cited

U.S. PATENT DOCUMENTS 4,665,176 A    5/1987   Hirai et al. .................... 544/4

FOREIGN PATENT DOCUMENTS

| EP | 0 347 749 | 12/1989 |
| EP | 0 487 097 | 5/1992 |

OTHER PUBLICATIONS

Toru Sugaya, "6H–Pyrazolo[4,5,1–de]acridin–6–ones as a Novel Class of Antitumor Agents. Synthesis and Biological Activity"; Journal of Medical Chemistry, pp. 1028–1032.
Journal of Pharmaceutical Sciences, vol. 61, No. 5 (May 1972), pp. 708–716.
Journal of Medicinal Chemistry, vol. 37, No. 7 (Apr. 1994), pp. 1028–1032.

*Primary Examiner*—Zinna Northington Davis
(74) *Attorney, Agent, or Firm*—Fitzpatrick, Cella, Harper & Scinto

(57) ABSTRACT

An aqueous solution of a pyrazoloacridone compound or pharmaceutical salt is stabilized using an acid, placing the solution in a well-closed container, evacuating air in the container, and sealing the container.

16 Claims, No Drawings

METHOD OF STABILIZING AQUEOUS PYRAZOLOACRIDONE DERIVATIVE SOLUTION

This application is a 371 of PCT/JP99/05643, filed Oct. 13, 1999.

TECHNICAL FIELD

The present invention relates to a method for stabilizing aqueous solutions containing a pyrazoloacridone derivative or a pharmaceutically acceptable salt thereof, and well-closed containers containing the aqueous solution.

BACKGROUND ART

Antioxidants are used to prevent drugs from oxidative decomposition. However, it is known that the antioxidants cannot be added to some drugs, since they would react with active ingredients or other additives in preparations (*J. Pharm. Sci.*, 61, 708 (1972)).

It is known that pyrazoloacridone derivatives have a DNA intercalation activity and exhibit an antitumor effect (*J. Med. Chem.*, 37, 1028 (1994)). Specific examples of such pyrazoloacridone derivatives are disclosed in Japanese Published Unexamined Patent Application No. 1064/93.

Pyrazoloacridone derivatives or pharmaceutically acceptable salts thereof are liable to decompose due to oxidation in aqueous solutions. Thus, there have been required stable aqueous solution preparations containing a pyrazoloacridone derivative or a pharmaceutically acceptable salt thereof which can be stored over a long period of time.

DISCLOSURE OF THE INVENTION

An object of the present invention is to provide a method for stabilizing aqueous solutions containing a pyrazoloacridone derivative or a pharmaceutically acceptable salt thereof, and well-closed containers containing the aqueous solution.

The present invention relates to a method for stabilizing aqueous solutions containing a pyrazoloacridone derivative or a pharmaceutically acceptable salt thereof, comprising adding an acid to an aqueous solution containing a pyrazoloacridone derivative represented by the following formula (I) (hereinafter referred to as Compound (I)):

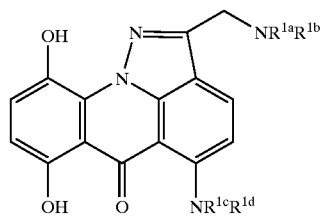

(I)

wherein $R^{1a}$, $R^{1b}$, $R^{1c}$ and $R^{1d}$ independently represent hydrogen, a lower alkyl group, —$(CH_2)_p$—X (wherein p is an integer of 1 to 6; and X represents a hydroxyl group, a lower alkoxy group, or —$NR^{2a}R^{2b}$ (wherein $R^{2a}$ and $R^{2b}$ independently represent hydrogen, a lower alkyl group, —$(CH_2)_m$—Y (wherein m is an integer of 1 to 6; and Y represents a hydroxyl group, a lower alkoxy group, or —$NR^{3a}R^3b$ (wherein $R^{3a}$, and $R^{3b}$ independently represent hydrogen or a lower alkyl group)), or $R^{2a}$ and $R^{2b}$ form a heterocyclic group together with the nitrogen atom adjacent thereto)), or —$CH((CH_2)_nOH)_2$ (wherein n is an integer of 1 to 5) or a pharmaceutically acceptable salt thereof; substituting the air in a well-closed container containing the aqueous solution with an inert gas; and sealing the container.

The present invention further relates to well-closed containers containing an aqueous solution containing Compound (I) or a pharmaceutically acceptable salt thereof and an acid, wherein the air in the well-closed container is substituted with an inert gas.

The lower alkyl group and the alkyl moiety in the lower alkoxy group in the definition of formula (I) include linear or branched alkyl groups having from 1 to 6 carbon atoms, such as methyl, ethyl, propyl, isopropyl, butyl, isobutyl sec-butyl, tert-butyl, pentyl, hexyl, and the like. The heterocyclic group formed together with the adjacent nitrogen atom includes pyrrolidinyl, piperidino, piperazinyl, morpholino, thiomorpholino, quinolyl, pyrimidinyl, pyridazinyl, pyridyl, pyrrolyl, imidazolyl, pyrazolyl, and the like. Among these, pyrrolidinyl, piperidino, piperazinyl and morpholino are preferred.

Examples of the pharmaceutically acceptable salt of Compound (I) include inorganic acid salts, such as hydrochlorides, hydrobromides, sulfates, phosphates, and the like, and organic acid salts, such as acetates, oxalates, malonates, maleates, fumarates, tartrates, succinates, citrates, and the like.

Compounds (I) are known compounds, which can be produced by, for example, the production method described in Japanese Published Unexamined Patent Application No. 1064/93.

The concentration of Compound (I) in the aqueous solution is preferably from 0.1 to 1,000 mM, more preferably from 1 to 100 mM, and particularly preferably from 10 to 50 mM.

Examples of Compound (I) are shown in Table 1.

TABLE 1

(I)

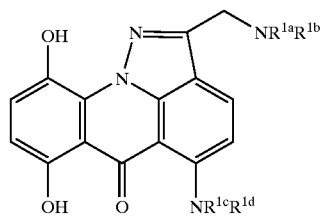

| Compound No. | $NR^{1a}R^{1b}$ | $NR^{1c}R^{1d}$ |
|---|---|---|
| 1 | $NH(CH_2)_2NH_2$ | $NH(CH_2)_2NH_2$ |
| 2 | $N(C_2H_5)_2$ | $NH(CH_2)_2NH_2$ |
| 3 | $N(C_2H_5)_2$ | $NH(CH_2)_2N(CH_3)_2$ |
| 4 | $NH(CH_2)_2OH$ | $NH(CH_2)_2NH_2$ |
| 5 | $NH(CH_2)_2OH$ | $NH(CH_2)_3NH_2$ |
| 6 | $NH(CH_2)_2OH$ | $NH(CH_2)_2NH(CH_2)_2OH$ |
| 7 | $NH(CH_2)_2OH$ | $NH(CH_2)_2NHCH_3$ |
| 8 | $NH(CH_2)_2OH$ | $NH(CH_2)_2N(CH_3)_2$ |
| 9 | $N[(CH_2)_2OH]_2$ | $NH(CH_2)_2N(CH_3)_2$ |
| 10 | $NHCH(CH_2OH)_2$ | $NH(CH_2)_2NH_2$ |
| 11 | $NH(CH_2)_2OCH_3$ | $NH(CH_2)_2NH_2$ |
| 12 | $NHCH(CH_2OH)_2$ | $NH(CH_2)_2NH(CH_2)_2OH$ |
| 13 | $NHCH(CH_2OH)_2$ | $NH(CH_2)_3NH_2$ |
| 14 | $NHCH(CH_2OH)_2$ | $NH(CH_2)_2$—N⟨morpholino⟩ |

Examples of the acid include inorganic acids, organic acids, and inorganic salts thereof.

Examples of the inorganic acid include phosphoric acid, hydrochloric acid, sulfuric acid, nitric acid, and the like.

Examples of the organic acid include organic acids represented by the following formula (II) (hereinafter referred to as Compound (II)):

$$R^4R^5CH-COOH \quad (II)$$

wherein $R^4$ represents hydrogen or hydroxy; and $R^5$ represents hydrogen, carboxy, or alkyl having from 1 to 3 carbon atoms which may be substituted with hydroxy or carboxy. Examples of the alkyl having from 1 to 3 carbon atoms in the definition of formula (II) include methyl, ethyl, propyl, isopropyl, and the like. The substitution number of the hydroxy or carboxy is 1 or 2. Examples of Compound (II) include lactic acid, glyceric acid, tartronic acid, malic acid, tartaric acid, and the like. Lactic acid is particularly preferred as the organic acid.

Examples of the inorganic acid salt include alkali metal salts, such as lithium salts, sodium salts, potassium salts, and the like; and alkaline earth metal salts, such as beryllium salts, magnesium salts, calcium salts, and the like.

The concentration of the acid in the aqueous solution is preferably from 1 to 1,000 mM, more preferably from 5 to 500 mM, and particularly preferably from 10 to 200 mM.

The material and shape of the well-closed container is not particularly limited, so long as it can prevent the permeation of oxygen. Examples of such material include glass, metals, resins, and the like. Examples of the resin include polyethylene, polystyrene, polycarbonate, polypropylene, polyvinyl chloride, 6-nylon, polyethylene terephthalate, and the like, with a resin having a small coefficient of oxygen permeation being preferred. Examples of the resin having a small coefficient of oxygen permeation include resins having a coefficient of oxygen permeation less than $0.1 \times 10^{-11}$ cm$^3$ (STP) cm$^{-1}$s$^{-1}$cmHg$^{-1}$, such as polyvinyl alcohol, polyacrylonitrile, polyvinylidene chloride, and the like. Examples of such shape of the container include an ampul, a vial, a syringe, and the like.

The pH of the aqueous solution is from 1 to 7, preferably from 2 to 6, and particularly preferably from 3 to 5. The pH can be adjusted using an alkali, such as sodium hydroxide, potassium hydroxide, or the like, or an inorganic acid, such as hydrochloric acid, sulfuric acid, or the like.

The aqueous solution can contain a pharmaceutically acceptable antioxidant, solubilizing agent, isotonizing agent, surfactant, soothing agent, and the like, if desired. Examples of the antioxidant include ascorbic acid, vitamin E, L-cysteine, and the like. Examples of the solubilizing agent include polyethylene glycol and the like. Examples of the isotonizing agent include glycerine, glucose, sodium chloride, and the like. Examples of the surfactant include HCO-60 (manufactured by Nikko Chemicals Co., Ltd.), and the like. Examples of the soothing agent include benzyl alcohol, lidocaine, and the like.

Examples of the inert gas include a nitrogen gas, an argon gas, a helium gas, carbon dioxide, and the like. Among these, a nitrogen gas is preferred.

The substitution of the air in the well-closed container with the inert gas can be carried out by a conventional method. For example, the inert gas may be poured after the well-closed container is depressurized by drawing off the air therein with a vacuum pump or the like. Alternatively, the aqueous solution can be poured into the container in an inert gas atmosphere. Thus, the expression "substituting the air in a well-closed container containing the aqueous solution with an inert gas" as used in the present specification includes methods wherein the aqueous solution is poured into the container in an inert gas atmosphere, followed by sealing, and the expression "the air in the well-closed container is substituted with an inert gas" includes conditions wherein the aqueous solution is poured into the container in the inert gas atmosphere, followed by sealing. When the air in the container is substituted with the inert gas, it is preferred that the inert gas concentration in the gas in the container is increased to 90% (v/v) or more. In the present invention, the inert gas concentration in the gas in the container is more preferably 95% (v/v) or more, and particularly preferably 99% (v/v) or more. The concentration of the inert gas in the gas in the container can be determined by directly measuring the inert gas concentration by a known method or by measuring the oxygen gas concentration. The concentration of oxygen in the gas can be measured, for example, using a trace oxygen analyzer RO-102-SP (manufactured by Iijima Electronics Corporation).

Hereinafter, Examples, Comparative Examples and Test Examples of the present invention are shown. However, the present invention is not limited to these Examples. A concentration (%) of nitrogen is shown by v/v.

BEST MODE FOR CARRYING OUT THE INVENTION

Example 1

In water for injection, 50 mg of Compound 5 and 9 mg of lactic acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Example 2

In water for injection, 50 mg of Compound 5 was dissolved. After adjusting the pH to 4 by adding hydrochloric acid thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Example 3

In water for injection, 50 mg of Compound 5 and 9 mg of lactic acid were dissolved. After adjusting the pH to 6 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Example 4

In water for injection, 50 mg of Compound 5 and 6 mg of acetic acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Example 5

In water for injection, 50 mg of compound 5 and 13.6 mg of potassium dihydrogenphosphate were dissolved. After adjusting the pH to 4 by adding hydrochloric acid thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Example 6

In water for injection, 50 mg of Compound 5 and 15 mg of tartaric acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Using a freeze-dryer, the freeze-dry container was depressurized, and then a nitrogen gas was poured to substitute the air in the space of each vial with a nitrogen gas. After pouring the nitrogen gas, the vials were sealed with rubber stoppers and aluminum caps to produce an aqueous solution preparation of Compound 5. When analyzed with a trace oxygen analyzer RO-102-SP (manufactured by Iijima Electronics Corporation), the nitrogen concentration in the gas in the space of the vial was 99.5%.

Comparative Example 1

In water for injection, 50 mg of Compound 5 and 9 mg of lactic acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 2

In water for injection, 50 mg of Compound 5 was dissolved. After adjusting the pH to 4 by adding hydrochloric acid thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 3

In water for injection, 50 mg of Compound 5 and 9 mg of lactic acid were dissolved. After adjusting the pH to 6 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 4

In water for injection, 50 mg of Compound 5 and 6 mg of acetic acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 5

In water for injection, 50 mg of Compound 5 and 21 mg of citric acid were dissolved. After adjusting the pH to 4 by adding sodium hydroxide thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 6

In water for injection, 50 mg of Compound 5 and 13.6 mg of potassium dihydrogenphosphate were dissolved. After adjusting the pH to 4 by adding hydrochloric acid thereto, the total volume was made up to 10 mL. The solution was aseptically filtered through a sterile filter (0.22 µm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Comparative Example 7

In water for injection, 50 mg of Compound 5 and 15 mg of tartaric acid were dissolved. After adjusting the pH to 4 by adding sodium hydroxide thereto, the total volume was made up to 10 mL. The solution was aseptically filtered through a sterile filter (0.22 μm, Acrodisc manufactured by Gelman Science), and a 1 mL portion each of the solution was poured in glass vials. Then, the vials were sealed with rubber stoppers and aluminum caps to produce an aqueous solution preparation of Compound 5.

Test Example 1

The aqueous solution preparations produced in the above Examples 1 to 6 and Comparative Examples 1 to 7 were stored in a thermostat at 60° C. for 60 days. The residual ratio of Compound 5 was measured by high performance liquid chromatography.

Analytical conditions for high performance liquid chromatography:

Column: YMC-Pack ODS-AM AM-312

Mobile phase: 0.1 M phosphate buffer (pH 3.0) containing 10 mM 1-octanesulfonic acid:acetonitrile (73:27, w/w)

Flow rate: 1.5 mL/min

Detection wavelength: 267 nm

The results are shown in Table 2.

TABLE 2

| | Residual ratio of Compound 5 (%) |
|---|---|
| Example 1 | 91.7 |
| Example 2 | 81.5 |
| Example 3 | 73.3 |
| Example 4 | 89.4 |
| Example 5 | 88.3 |
| Example 6 | 92.7 |
| Comparative Example 1 | 26.9 |
| Comparative Example 2 | 38.9 |
| Comparative Example 3 | 16.2 |
| Comparative Example 4 | 30.5 |
| Comparative Example 5 | 16.0 |
| Comparative Example 6 | 36.8 |
| Comparative Example 7 | 21.8 |

Test Example 2

The aqueous solution preparations produced in the above Examples 1 to 6 and Comparative Examples 1 to 7 were stored in a thermostat at 60° C. for 60 days. Then the coloration and dissolution conditions of each aqueous solution were observed with the naked eye.

The results are shown in Table 3.

TABLE 3

| | Change in coloration | Dissolution condition |
|---|---|---|
| Example 1 | − | Clear |
| Example 2 | ++ | Clear |
| Example 3 | ++ | Clear |
| Example 4 | + | Clear |
| Example 5 | + | Clear |
| Example 6 | + | Slightly cloudy |
| Comparative Example 1 | +++ | Clear |
| Comparative Example 2 | +++ | Clear |
| Comparative Example 3 | +++ | Clear |
| Comparative Example 4 | +++ | Clear |
| Comparative Example 5 | +++ | Oily and very cloudy |

TABLE 3-continued

| | Change in coloration | Dissolution condition |
|---|---|---|
| Comparative Example 6 | +++ | Clear |
| Comparative Example 7 | +++ | Oily and very cloudy |

Score of change in coloration
−: No change.
+: Slight increase in coloration is observed.
++: Noticeable increase in coloration.
+++: Highly noticeable increase in coloration.

INDUSTRIAL APPLICABILITY

According to the present invention, aqueous solution preparations containing a pyrazoloacridone derivative or a pharmaceutically acceptable salt thereof can be stored at stable conditions over a long period of time.

What is claimed is:

1. A method for stabilizing an aqueous solution containing a pyrazoloacridone compound or a pharmaceutically acceptable salt thereof, comprising:

adding an acid to a container of an aqueous solution comprising a pyrazoloacridone compound represented by formula (I):

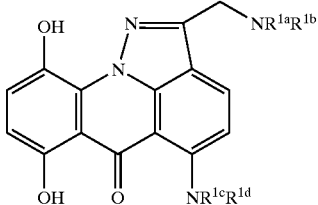

(I)

wherein $R^{1a}$, $R^{1b}$, $R^{1c}$ and $R^{1d}$ independently represent hydrogen, a lower alkyl group, —$(CH_2)_p$—X (wherein p is an integer of 1 to 6; and X represents a hydroxyl group, a lower alkoxy group, or —$NR^{2a}R^{2b}$ (wherein $R^{2a}$ and $R^{2b}$ independently represent hydrogen, a lower alkyl group, —$(CH_2)_m$—Y (wherein m is an integer of 1 to 6; and Y represents a hydroxyl group, a lower alkoxy group, or —$NR^{3a}R^{3b}$ (wherein $R^{3a}$ and $R^{3b}$ independently represent hydrogen or a lower alkyl group)), or $R^{2a}$ and $R^{2b}$ form a heterocyclic group together with the nitrogen atom adjacent thereto)), or —$CH((CH_2)_nOH)_2$ (wherein n is an integer of 1 to 5) or a pharmaceutically acceptable salt thereof;

evacuating air from the container; and sealing the container.

2. The method as claimed in claim 1, wherein the acid is an organic acid represented by the following formula (II):

$$R^4R^5CH-COOH \qquad (II)$$

wherein $R^4$ represents hydrogen or hydroxy; and $R^5$ represents hydrogen, carboxy, or alkyl having from 1 to 3 carbon atoms which may be substituted with hydroxy or carboxy.

3. The method as claimed in claim 1, wherein the acid is lactic acid.

4. The method as claimed in any of claims 1 to 3, wherein the aqueous solution has a pH of 2 to 6.

5. A well-closed container comprising an aqueous solution containing a pyrazoloacridone compound represented by formula (I):

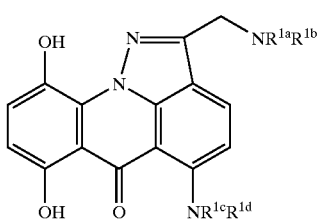
(I)

wherein $R^{1a}$, $R^{1b}$, $R^{1c}$ and $R^{1d}$ independently represent hydrogen, a lower alkyl group, —$(CH_2)_p$—X (wherein p is an integer of 1 to 6; and X represents a hydroxyl group, a lower alkoxy group, or —$NR^{2a}R^{2b}$ (wherein $R^{2a}$ and $R^{2b}$ independently represent hydrogen, a lower alkyl group, —$(CH_2)_m$—Y (wherein m is an integer of 1 to 6; and Y represents a hydroxyl group, a lower alkoxy group, or —$NR^{3a}R^{3b}$ (wherein $R^{3a}$ and $R^{3b}$ independently represent hydrogen or a lower alkyl group)), or $R^{2a}$ and $R^{2b}$ form a heterocyclic group together with the nitrogen atom adjacent thereto)), or —$CH((CH_2)_nOH)_2$ (wherein n is an integer of 1 to 5), or a pharmaceutically acceptable salt thereof, and an acid, wherein an atmosphere in the well-closed container does not contain air.

6. The well-closed container as claimed in claim 5 wherein said acid is an organic acid represented by the following formula (II):

$$R^4R^5CH—COOH \qquad (II)$$

wherein $R^4$ represents hydrogen or hydroxy; and $R^5$ represents hydrogen, carboxy, or alkyl having from 1 to 3 carbon atoms which may be substituted with hydroxy or carboxy.

7. The well-closed container as claimed in claim 5, wherein the acid is lactic acid.

8. The well known container as claimed in any of claims 5 to 7, wherein the aqueous solution has a pH of 2 to 6.

9. The method as claimed in any of claims 1 to 3, wherein the evacuated container is filled with an inert gas.

10. The method as claimed in claim 9, wherein the inert gas is nitrogen gas.

11. The method as claimed in claim 4, wherein the evacuated container is filled with an inert gas.

12. The well-closed container as claimed in any of claims 5–7, wherein the atmosphere inside the container is inert.

13. The well-closed container as claimed in claim 8, wherein the atmosphere inside the container is inert.

14. The well-closed container as claimed in claim 12, wherein the inert gas is nitrogen gas.

15. The well-closed container as claimed in claim 13, wherein the inert gas is nitrogen gas.

16. The method as claimed in claim 11, wherein the inert gas is nitrogen gas.

* * * * *

UNITED STATES PATENT AND TRADEMARK OFFICE
CERTIFICATE OF CORRECTION

PATENT NO.     : 6,552,198 B1
DATED          : April 22, 2003
INVENTOR(S)    : Yutaka Tomada et al.

It is certified that error appears in the above-identified patent and that said Letters Patent is hereby corrected as shown below:

<u>Column 9,</u>
Line 27, "5" should read -- 5, --.

<u>Column 10,</u>
Line 8, "well known" should read -- well-closed --.

Signed and Sealed this

Eighteenth Day of November, 2003

JAMES E. ROGAN
*Director of the United States Patent and Trademark Office*